(12) United States Patent
Alvarez (10) Patent No.: US 8,929,508 B1
(45) Date of Patent: Jan. 6, 2015

(54) ENERGY SELECTIVE X-RAY SYSTEM WITH LOW NOISE

(76) Inventor: Robert E. Alvarez, Mountain View, CA (US)

( * ) Notice: Subject to any disclaimer, the term of this patent is extended or adjusted under 35 U.S.C. 154(b) by 348 days.

(21) Appl. No.: 13/448,856

(22) Filed: Apr. 17, 2012

(51) Int. Cl.
  *G01N 23/00* (2006.01)
  *G01D 18/00* (2006.01)
  *G01N 23/087* (2006.01)

(52) U.S. Cl.
  CPC .................................. *G01N 23/087* (2013.01)
  USPC .......................................... 378/18; 378/207

(58) Field of Classification Search
  USPC .................... 378/4, 18, 19, 62, 207
  See application file for complete search history.

(56) References Cited

U.S. PATENT DOCUMENTS

| | | | |
|---|---|---|---|
| 3,965,358 A | 6/1976 | Macovski | |
| 4,029,963 A | 6/1977 | Alvarez et al. | |
| 6,507,633 B1 | 1/2003 | Elbakri et al. | |
| 6,754,298 B2 | 6/2004 | Fessler | |
| 7,016,456 B2 * | 3/2006 | Basu et al. | 378/18 |
| 7,623,616 B2 | 11/2009 | Ziegler et al. | |
| 7,822,169 B2 | 10/2010 | Roessl et al. | |
| 7,950,849 B2 * | 5/2011 | Claus et al. | 378/207 |
| 8,315,352 B2 * | 11/2012 | Wu et al. | 378/5 |
| 2004/0030246 A1 * | 2/2004 | Townsend et al. | 600/427 |
| 2006/0109949 A1 * | 5/2006 | Tkaczyk et al. | 378/4 |
| 2010/0200558 A1 | 8/2010 | Wang et al. | |
| 2011/0052022 A1 * | 3/2011 | Xu et al. | 382/131 |

OTHER PUBLICATIONS

R. E. Alvarez, "Near optimal energy selective x-ray imaging system performance with simple detectors," Medical Physics vol. 37, pp. 822-841, (Feb. 2010).
R.E. Alvarez, "Estimator for Photon Counting Energy Selective X-ray Imaging with Multi-bin Pulse Height Analysis" Medical Physics, vol. 38, pp. 2324-2334 (May 2011).
R. E. Alvarez and A. Macovski, "Energy-selective reconstructions in x-ray computerized tomography," Physics in Medicine and Biology vol. 21, pp. 733-744, (1976).
E. Roessl and R. Proksa, "K-edge imaging in x-ray computed tomography using multi-bin photon counting detectors," Physics in Medicine and Biology vol. 52, pp. 4679-4696, (2007).
J. P. Schlomka, et al., "Experimental feasibility of multienergy photon-counting K-edge imaging in pre-clinical computed tomography," PhysMedBiol vol. 53,pp. 4031-4047(2008).
M. J. Tapiovaara and R. Wagner, "SNR and DQE analysis of broad spectrum x-ray imaging," Physics in Medicine and Biology vol. 30, pp. 519-529, (1985).

* cited by examiner

*Primary Examiner* — Irakli Kiknadze (57) ABSTRACT

An apparatus or method for providing information about an object from x-ray radiation transmitted through the object. An embodiment comprises an x-ray source (10) positioned on one side of an object (50) an x-ray detector (102) positioned on the opposite side, and means for computing two or more information signals, which are substantially the line integrals of the basis set coefficients of the x-ray attenuation coefficient from the x-ray photons transmitted through said object at three or more regions of the x-ray energy spectrum. In one embodiment the means for computing the two or more information signals comprises a linear maximum likelihood estimator (122), a correction processor (142) to compute a correction to the linear maximum likelihood estimate (132), and an adder (152) to add the estimate and the correction to produce the two or more information signals (154).

13 Claims, 5 Drawing Sheets

ENERGY SELECTIVE X-RAY SYSTEM WITH LOW NOISE

CROSS-REFERENCE TO RELATED APPLICATIONS

This application claims the benefit of provisional patent application Ser. No. 61/434,927, filed 2011 Apr. 19 by the present inventor.

BACKGROUND OF THE INVENTION

Prior Art

| U.S. Patents | | |
| --- | --- | --- |
| Pat. No. | Issue Date | Patentee |
| 3,965,358 | Jun. 22, 1976 | Macovski |
| 4,029,963 | Jun. 14, 1977 | Alvarez et al. |
| 6,507,633 | Jan. 14, 2003 | Elbakri et al. |
| 6,754,298 | Jun. 22, 2004 | Fessler |
| 7,623,616 | Nov. 24, 2009 | Ziegler et al. |
| 7,822,169 | Oct. 26, 2010 | Roessl et al. |

| U.S. Patent Applications | | |
| --- | --- | --- |
| Application Ser. No. | Date | Patentee |
| 12/700,558 | Aug. 12, 2010 | Wang et al. |

Non-Patent Literature Documents

R. E. Alvarez, "Near optimal energy selective x-ray imaging system performance with simple detectors," *Medical Physics* 37, no. 2, 822-841, (February 2010)

R. E. Alvarez, "Estimator for Photon Counting Energy Selective X-ray Imaging with Multi-bin Pulse Height Analysis" *Medical Physics*, 38, pages 2324-2334 (May 2011)

R. E. Alvarez and A. Macovski, "Energy-selective reconstructions in x-ray computerized tomography," Physics in Medicine and Biology 21, 733-44, (1976)

E. Roessl and R. Proksa, "K-edge imaging in x-ray computed tomography using multi-bin photon counting detectors," Physics in Medicine and Biology 52, no. 15, 4679-4696, (2007)

J. P. Schlomka, E. Roessl, R. Dorscheid, S. Dill, G. Martens, T. Istel, C. Baumer, C. Herrmann, R. Steadman, G. Zeitler, A. Livne, and R. Proksa, "Experimental feasibility of multienergy photon-counting K-edge imaging in pre-clinical computed tomography," Physics in Medicine and Biology 53, no. 15, 4031-4047, (August 2008).

M. J. Tapiovaara and R. Wagner, "SNR and DQE analysis of broad spectrum x-ray imaging," Physics in Medicine and Biology vol. 30, 519-529, (1985)

This invention generally relates to systems for providing information about an object from x-ray radiation transmitted through the object.

X-rays have been used to provide information about the interior of an object since their discovery by Roentgen in 1896. In medicine, x-ray information is used to diagnose and evaluate diseases of the thorax, abdomen, breast, and extremities. X-ray transmission data can also be used to compute images of cross sections of the body with computed tomography and planar slices with planar tomography and tomosynthesis. The data are also used for non-imaging applications such as measuring bone calcification. In industry, x-ray information is used to monitor welds in cross-country pipelines, to measure product quality for process control in manufacturing, and to image the contents of baggage at airports. X-ray information is also used in many areas of scientific research such as biology or archaeology. In this patent the term "x-ray" will be used to refer to any kind of short wavelength electromagnetic radiation such as gamma rays produced by radioactive materials, synchrotron radiation produced by particle accelerators, and the radiation from high energy linear accelerators (linacs).

The first x-ray detector was photographic film. More recently electronic detectors have been introduced in CT scanners and flat panel detectors in digital radiography systems. All of these detectors respond to the sum of the energies of the x-ray photons. An alternative detector counts the total number of photons regardless of their energy.

Common sources of radiation, such as x-ray tubes, produce a broad spectrum of photon energies. Materials differ in the way that they transmit radiation of different energies and this variation provides information about the object that is not measured by detectors that only respond to the total energy or the total number of the photons. The paper by Tapiovaara and Wagner (Physics in Medicine and Biology Vol. 30, pp. 519-529, 1985) showed that measuring the energy spectrum can produce images with a larger signal to noise ratio (SNR) than systems that only measure the total energy or total number of photons. A larger SNR is desirable because it allows us to visualize smaller and more subtle features of the object at a lower x-ray dose. The improvement in SNR did not increase the dose to the patient.

U.S. Pat. No. 4,029,963 and the paper "Energy-selective Reconstructions in X-ray Computerized Tomography" (Physics in Medicine and Biology, VOL. 21, pp. 733-744, 1976) by the inventor of this patent and Albert Macovski showed an approach to extracting the energy information. The method relies on the fact that x-rays interact with matter in only a small number of fundamental processes such as the photoelectric interaction or Compton scattering. The probability of interaction for a fixed small thickness of a material is called the x-ray attenuation coefficient. Because of the physics of the x-ray interactions, Alvarez and Macovski were able to show that the x-ray attenuation coefficient is the sum of two functions of x-ray energy each multiplied by a separate number. Because the energy functions are known before hand, all of the information about the object is determined by the two numbers, which I call the basis set coefficients. These depend only on the physical characteristics of the material at each point in the object and not on the x-ray energy.

To apply this concept, it is useful to introduce mathematical notation. The x-ray attenuation coefficient is denoted by $\mu(x, y, z; E)$. This means that it is a function of the coordinates (x,y,z) in the object and of the x-ray photon energy E. Alvarez and Macovski showed that the x-ray attenuation coefficient is equal to a sum of two basis functions of energy $f_1(E)$ and $f_2(E)$ each multiplied by basis set coefficients that are a function only of the position (x,y,z) in the object $$\mu(x,y,z;E) = a_1(x,y,z) f_1(E) + a_2(x,y,z) f_2(E). \tag{1}$$

The basis functions $f_1(E)$ and $f_2(E)$ can represent the contributions of the photoelectric effect and Compton scattering or can be the x-ray attenuation coefficients of physical materials such as aluminum and plastic.

It is a fundamental law of x-ray physics that the probability of transmission decreases exponentially with the thickness of the object. Mathematically, the probability of transmission is $e^{-\int_P \mu(x,y,z;E)ds}$ where $\int_P \mu(x,y,z;E)ds$ is the line integral of the x-ray attenuation coefficient multiplied by the distance along a path P from the source to the detector. Substituting the two function representation (Eq. 1), the line integral is $$\int_P \mu(x,y,z;E)ds = A_1 f_1(E) + A_2 f_2(E)$$

where $A_1$ and $A_2$ are the line integrals of the basis set coefficients $$A_1 = \int_P a_1(x,y,z) ds$$

$$A_2 = \int_P a_2(x,y,z) ds$$

The basis set coefficients $a_1(x,y,z)$ and $a_2(x,y,z)$ describe the properties at a single point in the object while the line integrals $A_1$ and $A_2$ depend on the properties along a line through the object. The Alvarez-Macovski paper and U.S. Pat. No. 4,029,963 showed that the same mathematical algorithms used in computed tomography to reconstruct the cross-section of an object could be used to reconstruct maps of the $a_1(x,y,z)$ and $a_2(x,y,z)$ in the cross-section. Alternately, the $A_1$ and $A_2$ line integrals can be displayed directly to produce projection images similar to chest x-rays.

Prior approaches to U.S. Pat. No. 4,029,963 such as described in U.S. Pat. No. 3,965,358 issued to A. Macovski attempted to measure materials in the cross section but failed to recognize that the x-ray attenuation coefficient is the sum of only two functions of x-ray energy.

The system described in U.S. Pat. No. 4,029,963 used measurements of the x-ray photons transmitted through the object with two x-ray energy spectra $S_1(E)$ and $S_2(E)$ to solve for the line integrals $A_1$ and $A_2$.

$$I_1 = \int S_1(E) e^{-A_1 f_1(E) - A_2 f_2(E)} dE$$

$$I_2 = \int S_2(E) e^{-A_1 f_1(E) - A_2 f_2(E)} dE$$

In one embodiment, the U.S. Pat. No. 4,029,963 used a polynomial approximation to solve the equations. The approximation is more accurate if we use the logarithms of the data $L_1 = \log(I_1)$ and $L_2 = \log(I_2)$, which are easily computed with digital signal processing systems known to persons skilled in the art of signal processing. The polynomial approximations to $A_1$ and $A_2$ are $$A_1 = c_0 + c_1 L_1 + c_2 L_2 + c_3 L_1 L_2 + c_4 L_1^2 + c_5 L_2^2$$

$$A_2 = d_0 + d_1 L_1 + d_2 L_2 + d_3 L_1 L_2 + d_4 L_1^2 + d_5 L_2^2$$

Figure 2:
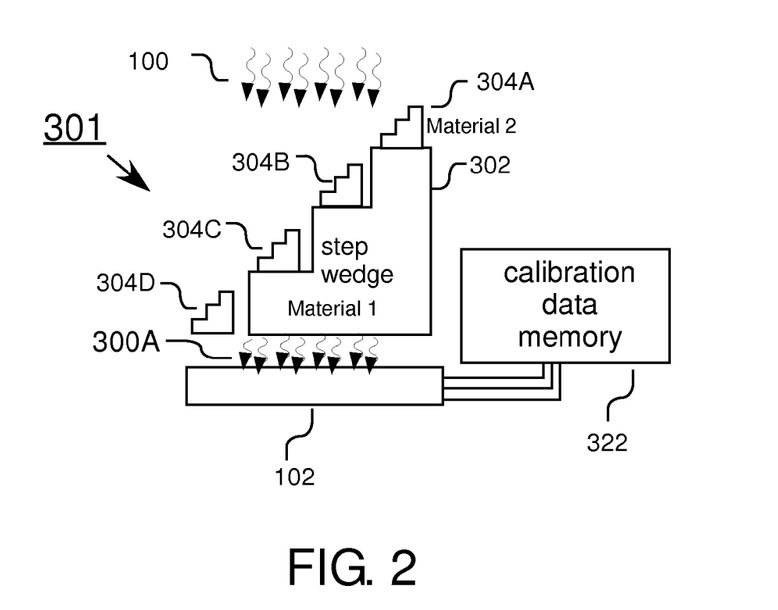
FIG. 2 is a calibrator to produce calibration data used to compute the linear maximum likelihood estimator coefficient and the correction data.

In the U.S. Pat. No. 4,029,963 the constants $c_0, c_1, \ldots$ and $d_0, d_1, \ldots$ are determined from analytical models of the x-ray spectra or preferably by measurements of a calibration phantom with known materials and thicknesses. For example, the calibration phantom can be made from twelve or more accurately machined thicknesses of samples of two materials with known $a_1$ and $a_2$. The measurements provide a set of accurately known $A_1$ and $A_2$ line integrals and the corresponding $L_1$ and $L_2$ values. These can be used with a least squares fitting algorithm such as is known to practioners skilled in the art to compute the constants $c_0, c_1, \ldots$ and $d_0, d_1, \ldots$ . An example of a calibration phantom is shown in FIG. 2. It can be used to make measurements periodically to ensure that the data used in the processing are accurate. Since the x-ray photons passing through an object in an x-ray imaging system are nearly parallel, we can obtain measurements with many combinations of thicknesses with step wedges with different step thicknesses. The data from individual pixels or detectors behind an individual step can be averaged together to provide low noise measurements to be used for calibration. As shown in FIG. 2, smaller step wedges of a different material can be placed on the larger step wedges to provide combinations of different thicknesses of the two materials.

U.S. Pat. No. 4,029,963 used only two spectra because we did not realize that more than two spectra could increase SNR. Making measurements with more than two spectra requires new methods to solve for the $A_1$ and $A_2$ line integrals that are not described by U.S. Pat. No. 4,029,963.

Measurements with multiple spectra can be acquired by energy-selective detectors or by changing the spectrum of the x-ray source and making multiple sequential measurements. In addition, a combination of changing the spectrum and measuring with an energy-selective detector can be used.

Recently, advances in x-ray sensor materials and digital electronics have made feasible x-ray detectors that count individual photons with the very large count rates encountered in medical imaging systems. Counting detectors have important practical advantages over the detectors currently used including lower noise and wider dynamic range. In addition, they provide a way to make measurements of the energy spectrum of the x-ray photons using pulse height analysis.

Pulse height analysis is a well known art but it is only recently that digital electronics has advanced so it can be done at high count rates. The concept of pulse height analysis is described in U.S. Pat. No. 2,529,666 issued to M. L. Sands in 1950. Detectors with pulse height analysis use a sensor that produces an electrical pulse signal for each individual photon. The amplitude or height of the pulse is proportional to the energy of the photon. In the pulse height analyzer, electronic circuits count the number of individual pulses during the exposure, which gives an indication of the amount of radiation incident on the detector, and also measure the pulse height of each photon. The circuits sort the amplitudes of the photon signals into separate bins and count the number that fall into each bin. The bins correspond to different regions of the energy spectrum. The counts in each of the bins during the exposure time are therefore indicative of the spectrum of the radiation.

The data in each bin correspond to the transmission through the object with a separate spectrum so photon counting detectors can provide many more than two spectra. My article "Near optimal energy selective x-ray imaging system performance with simple detectors," (R. E. Alvarez, Medical Physics vol. 37, pp. 822-841, 2010), shows that measurements with a larger number of spectra may be used to increase the signal to noise ratio without increasing dose. Obtaining the most information with a lower dose is important for medical applications since dose is potentially harmful. In many non-medical applications dose reduction is also important since dose can damage inspected objects such as electronic equipment in baggage. In addition, a system requiring less dose can use less powerful x-ray sources thus reducing the cost and size.

A possible approach is to solving for $A_1$ and $A_2$ from measurements with multiple energy spectra is to use multinomials. For example, with three measurements the second order multinomial is $$A_1 = c_0 + c_1 L_1 + c_2 L_2 + c_3 L_3 + c_4 L_1 L_2 + c_5 L_1 L_3 + c_6 L_2 L_3 + c_7 L_1^2 + c_8 L_2^2 + c_9 L_3^2$$

$$A_2 = d_0 + d_1 L_1 + d_2 L_2 + d_3 L_3 + d_4 L_1 L_2 + d_5 L_1 L_3 + d_6 L_2 L_3 + d_7 L_1^2 + d_8 L_2^2 + d_9 L_3^2$$

Where $L_1, L_2$, and $L_3$ are the logarithms of the counts in the three energy bins of the pulse height analyzer and $c_0, c_1, \ldots$ and $d_0, d_1, \ldots$ are constants.

This has the advantage that the computation is fast. In addition, the constants $c_0, c_1, \ldots$ and $d_0, d_1, \ldots$ can be determined from measurements on a calibration phantom using least squares so it does not require measurements the x-ray spectrum and energy response.

The multinomial approach, however, results in much higher noise in $A_1$ and $A_2$ compared with the method of this invention. This is shown in my article, "Estimator for Photon Counting Energy Selective X-ray Imaging with Multi-bin Pulse Height Analysis" (R. E. Alvarez, *Medical Physics*, Vol. 38, pages 2324-2334, May 2011). The article shows that the noise with a multinomial can be hundreds of times larger than with the maximum likelihood estimator implemented in this invention. Higher noise is undesirable in x-ray systems because it limits the ability to discern small objects or small differences in object properties.

Another approach to determining the $A_1$ and $A_2$ line integrals from the logarithms of the counts data is to do a table look up. This is a well-known method to persons skilled in the art of signal processing. The table look up method relies on a set of accurately known measurements of the interpolated quantity, the line integrals in our case, at a set of measured data points, the logarithms of the counts data. These could be obtained from measurements of a calibration phantom as described previously. The data can be arranged in a table, which is two-dimensional for two PHA bins, or three-dimensional for three bins, etc. The signal processor computes the values of the $A_1$ and $A_2$ line integrals by interpolating between the data points in the tables with the measured data for each point in the image.

The accuracy of table look up methods depends on the spacing of the data in the table, which, in turn, depends on the size of the table. In addition, the speed of the table lookup depends in whether the data are equally spaced and on the dimensionality of the data. There are fast and accurate methods for interpolation with equally spaced data as known by practioners skilled in the art. For example, the multi-dimensional extension of linear interpolation is fast and accurate. However, table look-up with non-equally spaced data is difficult and less accurate.

The logarithms of the x-ray data are not equally spaced for a calibration phantom with equal step heights. We could conceivably use unequal step heights to provide equal spaced logarithm of counts data but this would only be valid for a fixed x-ray tube voltage and detector response. This cannot be done since, in general, x-ray systems need to operate at more than one tube voltage.

Another approach is to pre-compute an equally spaced table by interpolating from the unequally spaced data. This can be done using Lagrange interpolation to compute the data at the missing points in an equally spaced table from the unequally spaced data.

Another problem with table look up is that the number of data points increases geometrically with the dimension of the table, which is the number of energy spectra. The dimension complicates the algorithm and also increases the complexity of the calibration phantom. For example, if 100 points provide sufficient accuracy with one spectrum data, ten thousand points are required to provide the same accuracy with two spectra and one million points are required for three spectra, and so on. The problem with unequally spaced data is compounded with higher dimensional data.

An additional problem is that the output of the table look up process may not be the optimal value to minimize the noise variance. As we have seen with polynomial interpolation, simply computing values that are accurate for very low noise data from a physical phantom does not necessarily produce data with low noise variance. We need to take into account the variance of the noise in each of the measurements and also their correlation.

The computation of the $A_1$ and $A_2$ line integrals from data with noise is an example of statistical estimation. Statistical estimators have been studied for many years and an optimal method called a maximum likelihood estimator has been developed as is well known to practioners skilled in the art. The maximum likelihood estimator can achieve a noise variance equal to a fundamental lower limit called the Cramer-Rao lower bound. This lower limit is important because once we have developed an estimator that has this noise variance, we know that we can do no better with any other estimator.

Prior implementations of a maximum likelihood estimator for x-ray energy spectrum information required an iterative, successive approximation method. For example, Roessl and Proksa ("K-edge imaging in x-ray computed tomography using multi-bin photon counting detectors," Phys Med Biol 52, 4679-4696, 2007) describe the theory of an iterative estimator and Schlomka et al. ("Experimental feasibility of multi-energy photon-counting K-edge imaging in pre-clinical computed tomography," Phys Med Biol, 53, 4031-4047, 2008) its experimental implementation.

The iterative method of Roessl and Proksa achieves the Cramer-Rao lower bound but it has substantial problems. Iterative methods can potentially fail to converge and have long, unpredictable computation times. If the method fails to converge the results will have large errors. The unpredictable computation time is a severe problem with a "real-time" system like X-ray imaging systems. A real-time system has to process the data for one measurement before the next measurement is acquired. If the computation time is long and unpredictable then either the system has to be slowed to accommodate the longest possible computation time or an error will occur if the computation is not finished before the next measurement arrives. Slow data acquisition can lead to errors with moving objects such as breathing or heart motion in medical imaging or objects on conveyor belts such as in manufacturing or baggage screening.

Another problem with the iterative method is that it requires measurements of the energy spectrum and the energy response of each pulse height analysis energy bin. These measurements use specialized instruments and techniques and would be difficult to carry out in a clinical environment. However, due to aging of components and other effects, the spectra and detector response may change with time and the spectral response must be measured periodically to ensure accurate and reliable data.

If we use a linear approximation to the relationship between the logarithm of the pulse height analyzer count signals and the $A_1$ and $A_2$ line integrals, then we can implement the maximum likelihood estimator as a matrix multiplication. Modern signal processing electronics can execute matrix multiplications extremely rapidly and with a fixed, predictable time. Although the linear model has many computation and implementation advantages, it is only accurate for data close to the operating point $[L_0, A_0]$. If we use it for data not near that point, the results may be inaccurate.

A problem with medical applications of conventional radiography is that x-ray shadows of overlying body structures can interfere with the image of the structures of interest. Physicians have developed methods to make relevant structures visible by injecting contrast agents with high x-ray attenuation into these regions. This makes it possible to view body structures that are otherwise not visible. For example, contrast agent is injected to increase the visibility of coronary arteries in the heart during cardiac angiography. With conventional x-ray systems without energy information, images are made before and after administering the contrast agent and then subtracted to show the regions where the contrast agent entered. However, with energy information, we do not have to subtract images taken at different times as in angiography. Instead, we can use a single measurement. This reduces motion artifacts with moving objects such as the beating heart.

The contrast material usually has high atomic number material so it x-ray attenuation coefficient cannot be represented by the two function decomposition in Eq. 1. This requires using three or more functions in the decomposition of the x-ray attenuation coefficient. An example with three function is $$\mu(x,y,z;E)=a_1(x,y,z)f_1(E)+a_2(x,y,z)f_2(E)+a_3(x,y,z)f_3(E).$$

The line integrals of the basis set coefficients $a_1, a_2, a_3 \ldots$ can be determined if three or more energy spectra are used by extending the two-dimensional results. With the vector notation, the vectors have dimensions of three or more and the matrices have higher dimensions but the method is otherwise the same. An iterative maximum likelihood estimator can be used but it has all the problems mentioned previously of long, varying computation time and possible failure to converge.

Alternative approaches to applying statistical estimation theory for extracting energy information such as U.S. Pat. No. 6,507,633 issued to Elbakri et al., U.S. Pat. No. 6,754,298 issued to Fessler and U.S. Pat. No. 7,623,616 issued to Ziegler et al. also use iterative methods and therefore also have these disadvantages.

U.S. patent application Ser. No. 12/700,558 by Wang and Pelc describes a method using two weighted sums of the detected energy spectra. This method requires an iterative likelihood maximization algorithm to compute the $A_1$ and $A_2$ line integrals, which Wang and Pelc implemented with the Matlab Optimization toolbox. This iterative method has the limitations of long and complex computation and unpredictable computation time described previously.

U.S. Pat. No. 7,822,169 describes a method to reduce noise by using the statistical properties of the data, the signal to noise ratios of the individual measurements. The method has several shortcomings First, it can only be applied with computed or linear tomography systems since it requires multiple measurements for each region-of-interest in the object. The method of the present invention can be applied to single projection systems as well as tomography systems. The U.S. Pat. No. 7,822,169 also only matches signal to noise ratios so it would not be expected to achieve the Cramer-Rao lower bound like the present invention.

SUMMARY

An object of the invention is a system to use data from x-ray measurements with multiple energy spectra to acquire information about an object. In one embodiment, the system computes the basis set coefficient line integrals from the measurements. A further object of the invention is a system that provides data with noise close to the Cramer-Rao lower bound. Another objective is a system that can compute the data rapidly and within a predictable time.

DRAWINGS

Figures

DRAWINGS

Figure 1:
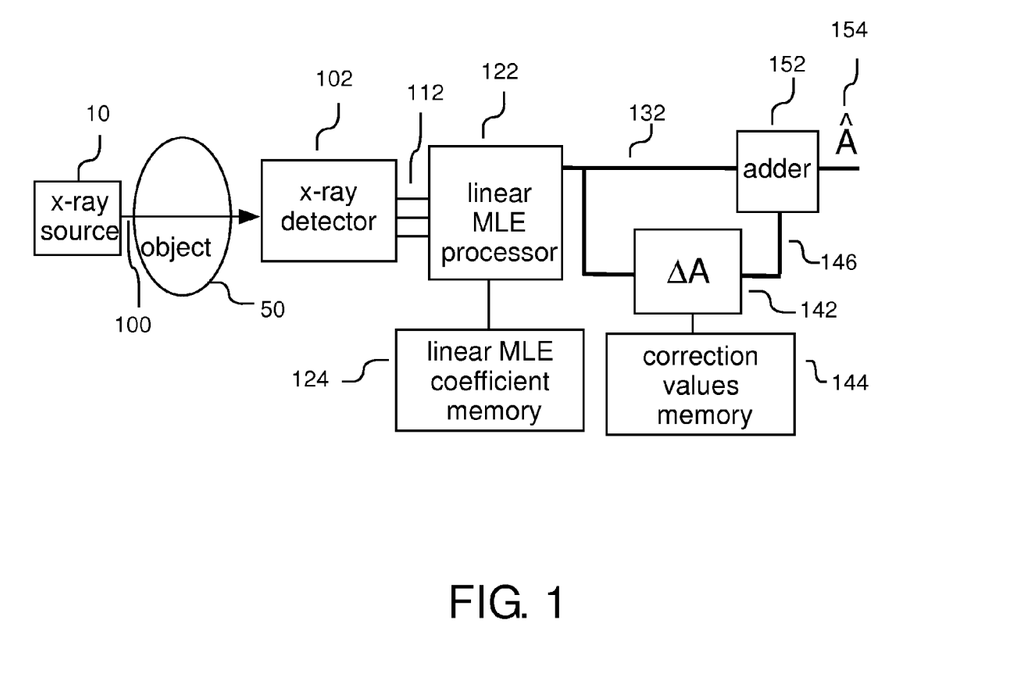
FIG. 1 is a block diagram of an x-ray system using the invention showing the signal flow from the incident radiation to the output A-vector.

Reference Numerals 10 x-ray source
50 object
100 x-ray radiation
102 x-ray detector
112 measurement data from x-ray detector
122 linear maximum likelihood estimator (MLE) processor
124 linear maximum likelihood estimator (MLE) coefficient memory
132 linear maximum likelihood estimate, denoted $\hat{A}_{MLE}$ in FIG. 1
142 correction processor
144 correction values memory
146 corrections data vector, denoted as AA in FIG. 1
152 adder
154 information signals, which are substantially the line integrals of basis set coefficients in x-ray attenuation coefficient representation, denoted $\hat{A}$ in FIG. 1
301 calibrator
302 material 1 step wedge
304A, 304B, 304C, 304D material 2 step wedges
322 calibration data memory
300A x-ray photons transmitted through calibrator
332 linear maximum likelihood estimator coefficient processor
402 correction data processor
501 three material calibrator
504B, 504C, 504D, 504E, 504F, 504G, 504H, 504I, 504J, 504K, 504L, 504M, 504N, 504O, 504P, 504Q third material step wedges
602 is a plot of the $A_1$ and $A_2$ values for calibrator 301
604 is an $A_1$ and $A_2$ point for a single step of calibrator 301
606 is the $\hat{A}_1$ and $\hat{A}_2$ values of the linear maximum likelihood estimate $\hat{A}_{MLE}$ for point 604
607 the operating point of calibrator
608 and 609 are the components of the corrections data vector $\hat{A}_{MLE}$ corresponding to point 604, denoted $\delta A_1$ and $\delta A_2$ in FIG. 5B

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures. It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent" versus "directly adjacent," etc.). The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved. Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly. Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

DETAILED DESCRIPTION

First Example Embodiment—FIG. 1

The block diagram in FIG. 1 shows an example embodiment. X-ray radiation photons 100 produced by x-ray source 10 are transmitted through object 50 and are incident on x-ray detector 102. The x-ray detector 102 produces signals indicative of the radiation in different bands of the spectrum. One embodiment of the x-ray detector 102 is a material such as ZnCdS with an applied electric field so it produces charge pulses whose amplitude is indicative of the energy of each detected x-ray photon. The pulse amplitudes are measured by a pulse height analyzer as described in U.S. Pat. No. 2,529,666.

The number of bins used for pulse height analysis depends on the method used to fabricate the detector, the number of detectors to be integrated into an assembly, the signal to noise ratio and dynamic range required for the application and other factors known to persons skilled in the art of pulse height analyzer design. The number used may vary depending on the application of the overall system so, for example, one choice would be optimal for a medical system and another for an industrial system.

Other embodiments for producing measurement data 112 of object 50 at multiple energy spectra such as making measurements sequentially with an x-ray source 10 that produces multiple spectra and a non-energy-resolving x-ray detector 102 are known to persons skilled in the art of x-ray measurements.

The measurement data 112 are inputs to the linear maximum likelihood estimator processor 122 (linear MLE processor in FIG. 1). The linear maximum likelihood estimator processor 122 is also connected to the linear MLE coefficient memory 124. The output of linear maximum likelihood estimator processor 122 is the signal 132. The signal 132 is connected to the adder 152 and the correction processor 142. The correction processor is also connected to the correction values memory 144. The output signal of the correction processor 142 is connected to the adder 152. The output of the adder is the estimate 154 denoted by Â in FIG. 1.

OPERATION

First Example Embodiment—FIGS. 1, 2, 3, 4, 6A, 6B, 6C, and 6D

The linear maximum likelihood estimator processor 122 produces a linear maximum likelihood estimate 132 for every measurement vector 112 of the x-ray detector. The linear maximum likelihood estimator is implemented as a matrix multiplication using a matrix whose entries are stored in the linear maximum likelihood estimator coefficient memory 124. The data in maximum likelihood estimator coefficient memory 124 are pre-determined and stored before the x-ray system is used to acquire data for an object.

We can describe the linear maximum likelihood estimator mathematically as follows. With multiple measurements and line integral signals it is convenient to organize the quantities as vectors, which are ordered sets of numbers and will be denoted here by bold face characters such as L, which is the vector of the logarithms of the pulse height analyzer bin counts L=[$L_1$, $L_2$, ... ]. Also, the line integrals are the vector A=[$A_1$, $A_2$], which I call the A-vector. In general, there is a non-linear relationship between L and A. This means that plots of the values of each component of A do not fall on multi-dimensional planes. However, the relationship between L and A is smooth and we can approximate it as linear for small deviations about an operating point [$L_0$, $A_0$]. If the deviations are δL and δA where L=$L_0$+δL and A=$A_0$+δA, the linear approximation to the non-linear relationship is $$\delta L = M \delta A + w$$

where M is a constant matrix, which can be computed as shown below, and w represents the measurement noise.

With this model, the maximum likelihood estimator is $$\hat{A}_{MLE} = [(M^T R^{-1} M)^{-1} M^T R^{-1}] L$$

where $M^T$ is the transpose of the matrix M and $R^{-1}$ is the inverse of the covariance matrix R. The transpose and inverse can be computed using methods known to persons skilled in numerical analysis.

The expression in brackets in this equation is complicated but it is a single matrix C, which can be pre-computed before the system is used and then stored in a digital memory to be applied during the use of the system by implementing the following equation $$\hat{A}_{MLE} = CL \quad (2)$$

The C matrix depends on the M matrix and the covariance matrix R, both of which can be pre-determined from measurements with the x-ray system of a calibration phantom.

An example of a calibrator is shown in FIG. 2 although other configurations are possible. The data required are the logarithms of the measured x-ray data for each of the combinations of step wedges 302 and 304A, 304B, 304C, 304D thicknesses. These are shown as 602 in FIG. 6A. The number of step wedges are for illustrative purposes only and other numbers may be used as determined by a person skilled in the art of signal processing to provide the data required for sufficient accuracy of the final $A_1$ and $A_2$ line integrals' values. The calibration data memory 322 stores the logarithms of the x-ray data for each of the steps in the calibrator wedges.

The data for the M matrix and the covariance matrix R are pre-determined from the measurements for a step in the calibration phantom with attenuation corresponding to an average for the objects to be examined by the system are used. The values of L and A for that step are called the operating point of the linear maximum likelihood estimator. The step is chosen to be an interior point 607 of the data for the calibrator 602 as shown in FIG. 6A.

Figure 6A:
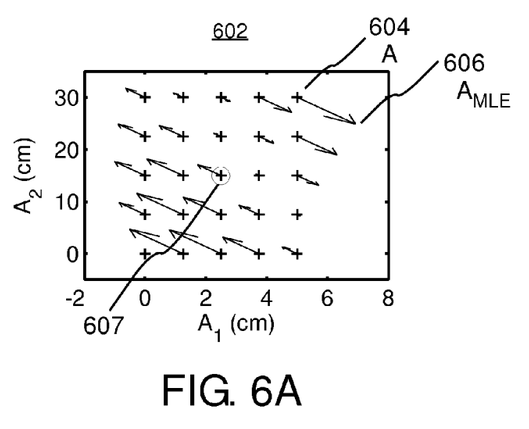
FIG. 6A shows the $A_1$ and $A_2$ points for a calibrator and the corresponding linear maximum likelihood estimates $\hat{A}_{MLE}$
Figure 6B:
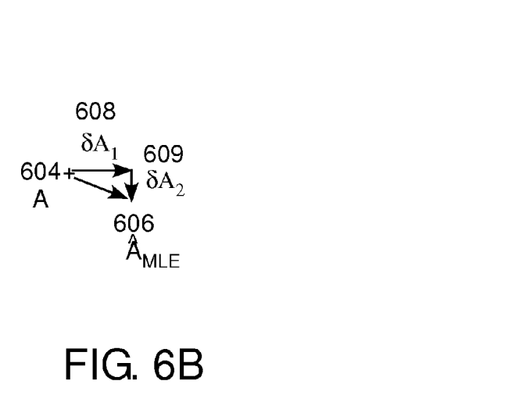
FIG. 6B shows a single $A_1$ and $A_2$ point, the corresponding linear maximum likelihood estimate and the components of the correction vector $\delta A_1$ and $\delta A_2$

The M matrix is the multidimensional gradient of the $A_1$ and $A_2$ for the operating point 607 in FIG. 6A and can be computed by taking differences of the surrounding data in the multidimensional space and dividing by the step offsets. Mathematically, this is $$M = -\Delta L / \Delta A$$

The covariance matrix R is computed from the data for operating point 607 in the calibration phantom data. The sizes of the individual steps in the calibration phantom are made big enough so there are multiple measurements by the x-ray system for step. The R matrix is then the sample covariance for the data $$R = \frac{1}{n-1} \sum_{k=1}^{n} (L_k - \bar{L})^2$$

Where n is the number of measurements, $L_k$ is an individual measurement, and $\bar{L}$ is the mean value of the measurements.

Figure 3:
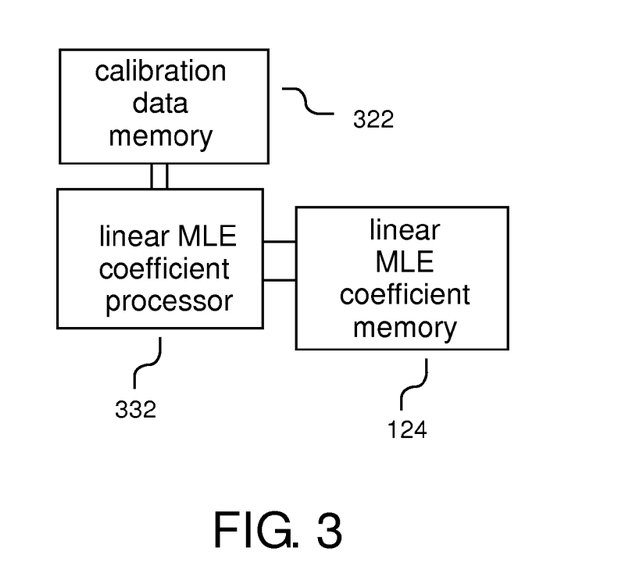
FIG. 3 is the linear maximum likelihood estimator coefficient processor.

An advantage is that using data from measurements of a calibration phantom with the x-ray system is much simpler for the user than measuring the tube spectrum and detector energy response as required for the iterative maximum likelihood estimator. The linear MLE coefficient processor 332 uses data stored in calibration data memory 322 to compute the linear MLE coefficient by implementing the following equation to compute the coefficients of the C matrix in Eq. 2. The coefficients are stored in linear MLE coefficient memory 124.

$$C = [(M^T R^{-1} M)^{-1} M^T R^{-1}]$$

The output of the linear maximum likelihood estimator processor 122 is the linear maximum likelihood estimate 132 and is denoted $\hat{A}_{MLE}$ in FIG. 1. Because a linear processor is used, the results will contain errors compared with the actual maximum likelihood estimator value. The errors are computed by the correction processor 142. This processor produces a corrections data vector 146 that is one input to the vector adder 152.

Figure 4:
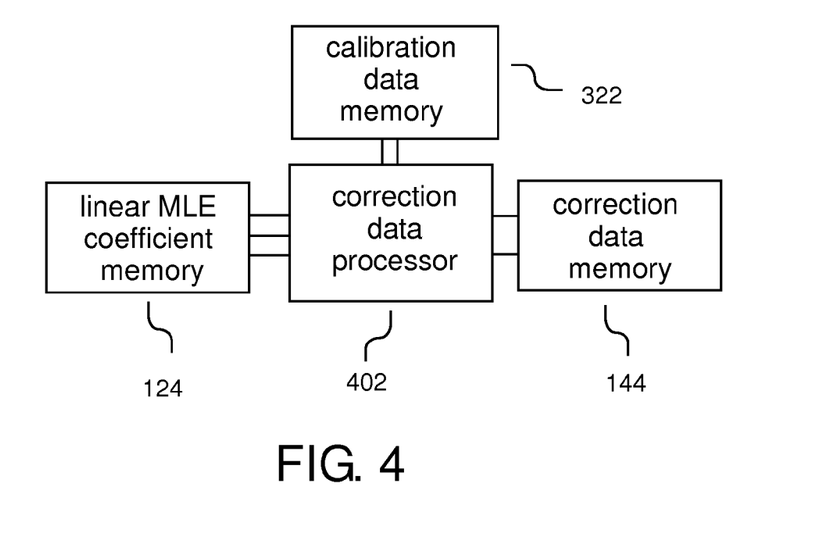
FIG. 4 is the correction data processor.

The corrections processor 142 uses data stored in the correction values memory 144. The data in the correction values memory 144 are computed from the data in the calibration data memory 322 and the data in the linear MLE coefficient memory 124 by the correction data processor 402.

The calculation can be better understood from FIGS. 6A, 6B, 6C, and 6D. Because of the construction of the calibrator, the calibrator data stored in calibration data memory 322 correspond to a set of known $A_1$ and $A_2$ line integrals plotted as 602 in FIG. 6A. The coordinates are determined by the thicknesses of the step wedges for each step. The correction data processor 402 computes the linear maximum likelihood estimate 606 for each step 604 from the data in calibration data memory 322. The difference between the known $A_1$ and $A_2$ line integrals for each step in the calibrator 301 and the linear maximum likelihood estimate for that step is the correction data vector with components 608 and 609. The correction data vectors for all the set of $A_1$ and $A_2$ line integrals 602 are stored in the correction values memory 144 after processing for equal spacing.

An equally-spaced data table is pre-computed from the calibrator data 602 by interpolation using Lagrange interpolation as is known to persons skilled in the art of signal processing. The computation of the equally spaced data is done only once when a new calibration data set is acquired and stored in the correction data memory 144 to be used by the x-ray system during the acquisition of image data.

Figure 6C:
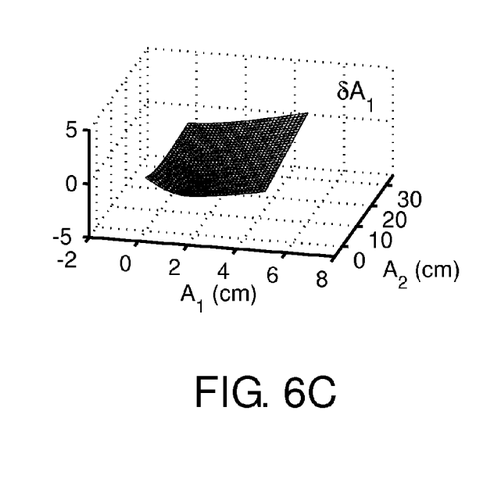
FIG. 6C shows the $\delta A_1$ component of the corrections vectors for the data in FIG. 6A
Figure 6D:
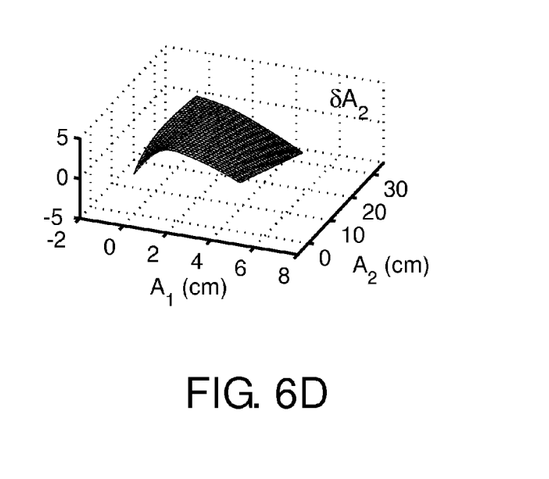
FIG. 6D shows the $\delta A_2$ component of the corrections vectors for the data in FIG. 6A

The corrections processor 142 computes the correction 146 by two-dimensional bi-linear interpolation of the linear maximum likelihood estimate 132 with the data in the correction values memory 144 using the method well known to persons skilled in the art of signal processing. The correction values memory data for each of the components are smooth as shown in FIGS. 6C and 6D so the calibrator step wedge thicknesses are pre-determined to give negligible two-dimensional bi-linear interpolation errors by methods known to persons skilled in the art of numerical computation.

The other input to the vector adder 152 is the linear maximum likelihood estimate 132. The vector adder 152 adds corresponding components of its inputs, which are the linear maximum likelihood estimate 132 and the corrections data vector 146 producing the output 154 denoted Â in FIG. 1, which is the two information signals representing the line integrals of the $a_1$ and $a_2$ basis set coefficients. The linear maximum likelihood estimator processor, correction processor 142, and the vector adder 152 can be implemented with digital signal processors with a stored program or by other methods known to persons skilled in the art of signal processing.

DETAILED DESCRIPTION

Figure 5:
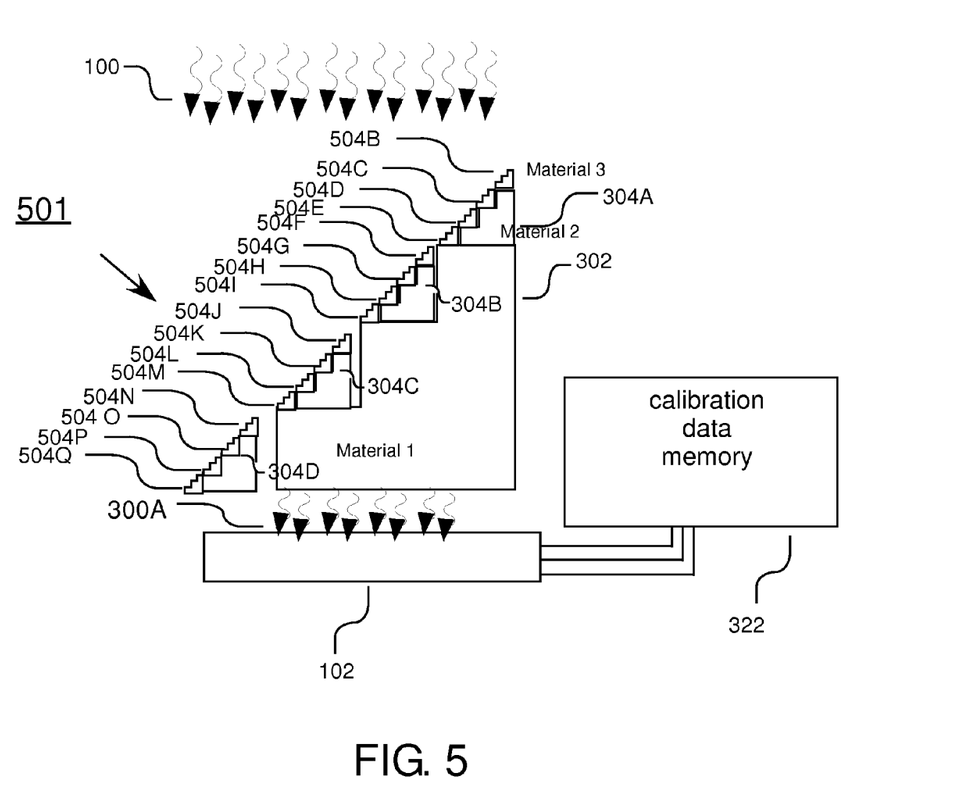
FIG. 5 shows a calibrator for a three basis function system as might be used with high atomic number contrast material.

Second Example Embodiment—FIG. 5

A second embodiment is shown in FIG. 4. This embodiment is used to provide information about the distribution of an externally administered contrast material in medical applications to enhance the visibility in body structures as would be familiar to a person skilled in the art of medical imaging. The contrast material is composed of high atomic number materials so it requires a three function basis set to represent its x-ray attenuation coefficient function. The use of a three function basis set results in three line integrals of the basis set coefficients. More than three functions may be used if there are several high atomic number elements in the contrast material but for this example embodiment three will be used.

The calibrator, shown in FIG. 5, has additional step wedges 504B, 504C, 504D, 504E, 504F, 504G, 504H, 504I, 504J, 504K, 504L, 504M, 504N, 504O, 504P, 504Q made of a third material. As an example, the third material can include the high atomic number elements such as iodine, gadolinium or other materials used in the externally administered contrast material embedded in a matrix of other materials to form a stable solid as would be known to persons skilled in the art of materials. For illustration, only the step wedges for a single additional material are shown but it is to be understood that additional layers of step wedges can be used with more than three materials.

OPERATION

Second Example Embodiment—FIG. 5

The operation of the second example embodiment parallels the operation of the first example embodiment described in the previous sections of this application. However, the linear maximum likelihood estimator processor 122, linear maximum likelihood estimator coefficient processor 332, correction data processor 402, the vector adder 152, the linear maximum likelihood estimator coefficient memory 124, the calibration data memory 322, and the correction data memory 144 would all be implemented with additional channels for the additional components of the A-vector. The processors and memory can be implemented with digital signal processors and digital electronic memory using methods known to persons skilled in the art of signal processing.

ADVANTAGES

The advantages of the invention are that it produces line integral data with lower noise and larger signal to noise ratio than systems using computation methods such as polynomial fits. In addition, the line integral values can be computed rapidly and with a fixed and known computation time. The computation can be done directly using digital signal processors without using iterative methods.

CONCLUSION, RAMIFICATIONS, AND SCOPE

While the above description contains many specificities, these should not be construed as limitations on the scope of any embodiment, but as exemplifications of the presently preferred embodiments thereof. Many other ramifications and variations are possible within the teachings of the various embodiments.

Thus the scope of the invention should be determined by the appended claims and their legal equivalents, and not by the examples given. The patent claims filed with the application are formulation proposals without prejudice for obtaining more extensive patent protection. The applicant reserves the right to claim even further combinations of features previously disclosed only in the description and/or drawings. The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods. References that are used in dependent claims indicate the further embodiment of the subject matter of the main claim by way of the features of the respective dependent claim; they should not be understood as dispensing with obtaining independent protection of the subject matter for the combinations of features in the referred dependent claims. Furthermore, with regard to interpreting the claims, where a feature is concretized in more specific detail in a subordinate claim, it should be assumed that such a restriction is not present in the respective preceding claims. Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium is adapted to store information and is adapted to interact with a data processing facility or computer device to execute the program of any of the above mentioned embodiments and/or to perform the method of any of the above mentioned embodiments. The computer readable medium or storage medium may be a built-in medium installed inside a computer device main body or a removable medium arranged so that it can be separated from the computer device main body. Examples of the built-in medium include, but are not limited to, rewrite-able non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

I claim:

1. Apparatus for providing information about an object from x-ray radiation transmitted through said object comprising:
   A. an x-ray source positioned on one side of said object producing an x-ray beam which transverses said object;
   B. an x-ray detector positioned on the side of said object opposite that of said x-ray source;
   C. means for computing two or more information signals, which are substantially the line integrals of the basis set coefficients in a representation of the x-ray attenuation coefficient at points along the line within said object, from the x-ray photons transmitted through said object at three or more regions of the x-ray energy spectrum,
   wherein said means for computing two or more information signals comprises means for computing a first approximation of said information signals and means for computing a correction to said first approximation and adder means for combining said first approximation and said correction to produce said two or more information signals.

2. The apparatus of claim 1 wherein said means for computing a first approximation of said information signals comprises means for computing a linear approximation to the maximum likelihood estimator.

3. The apparatus of claim 2 wherein said means for computing a linear approximation to the maximum likelihood estimator uses pre-determined linear maximum likelihood estimator coefficients computed from measurements of a calibration phantom measured with said x-ray source and said x-ray detector.

4. The apparatus of claim 1 wherein said means for computing a correction to said first approximation comprises means for interpolating in a table of pre-determined correction values using said first approximation as input.

5. The apparatus of claim 4 wherein said means for interpolating in a table of pre-determined correction values comprises a interpolating in a table of pre-determined values computed from measurements with a calibration phantom with said x-ray source and said x-ray detector and means for computing said pre-determined correction values from the measured data.

6. The apparatus of claim 1 wherein said means for measuring the x-ray photons transmitted through said object at three or more energy regions of the x-ray spectrum comprises means for changing the energy spectrum produced by said x-ray source to one of three or more pre-determined spectra and an x-ray detector means for measuring the total energy of transmitted x-ray photons with each of said pre-determined energy spectra produced by said x-ray source.

7. The apparatus of claim 1 wherein said means for measuring the x-ray photons transmitted through said object at three or more energy regions of the x-ray spectrum comprises means for changing the energy spectrum produced by said x-ray source to one of three or more pre-determined spectra and an x-ray detector means for measuring the total number of transmitted x-ray photons with each of said pre-determined energy spectra produced by said x-ray source.

8. The apparatus of claim 1 wherein said means for measuring the x-ray photons transmitted through said object at three or more energy regions of the x-ray spectrum comprises an energy-selective detector.

9. The apparatus of claim 8 wherein said x-ray detector is a photon counting detector with pulse height analysis.

10. A method for providing information about an object from x-ray radiation transmitted through said object comprising:
   A. providing an x-ray beam which transverses said object;
   B. measuring the x-ray photons transmitted through said object at three or more regions of the x-ray energy spectrum; and
   C. computing two or more information signals, which are substantially the line integrals of the coefficients in a representation of the x-ray attenuation coefficient at each point within said object, from said x-ray photons transmitted through said object at three or more regions of the x-ray energy spectrum,
   wherein said method for computing two or more information signals comprises computing a first approximation of said information signals, computing a correction to said first approximation and combining said first approximation and said correction to produce said two or more information signals.

11. The method of claim 10 wherein said method for computing a first approximation of said information signals comprises computing a linear maximum likelihood estimate from said x-ray photons transmitted through said object at three or more regions of the x-ray energy spectrum.

12. The method of claim 10 wherein said method for computing a correction to said first approximation comprises interpolating in a table of pre-determined correction values using said first approximation of said information signals as input.

13. The method of claim 10 wherein said method combining said first approximation and said correction to produce said two or more information signals comprises a method for adding corresponding components of said first approximation and said correction.

* * * * *